US010302656B2

(12) United States Patent
Krizman et al.

(10) Patent No.: US 10,302,656 B2
(45) Date of Patent: *May 28, 2019

(54) CMET PROTEIN SRM/MRM ASSAY

(71) Applicant: Expression Pathology, Inc., Rockville, MD (US)

(72) Inventors: David Krizman, Gaithersburg, MD (US); Todd Hembrough, Gaithersburg, MD (US); Sheeno Thyparambil, Frederick, MD (US)

(73) Assignee: Expression Pathology, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,912

(22) Filed: May 16, 2016

(65) Prior Publication Data

US 2016/0252525 A1 Sep. 1, 2016

Related U.S. Application Data

(63) Continuation of application No. 13/976,956, filed as application No. PCT/US2011/067439 on Dec. 27, 2011, now Pat. No. 9,372,195.

(60) Provisional application No. 61/427,396, filed on Dec. 27, 2010.

(51) Int. Cl.
*G01N 33/74* (2006.01)
*G01N 30/88* (2006.01)
*G01N 33/483* (2006.01)
*G01N 33/68* (2006.01)

(52) U.S. Cl.
CPC ..... *G01N 33/6872* (2013.01); *G01N 33/4833* (2013.01); *G01N 33/68* (2013.01); *G01N 33/6848* (2013.01); *G01N 33/74* (2013.01); *G01N 2030/8831* (2013.01); *G01N 2333/71* (2013.01); *G01N 2333/82* (2013.01); *G01N 2560/00* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 7,473,532 B2 | 1/2009 | Darfler et al. | |
| 7,632,386 B2 | 12/2009 | Klein et al. | |
| 2004/0009568 A1 | 1/2004 | Mroczkowski et al. | |
| 2008/0159992 A1 | 7/2008 | Rotman et al. | |
| 2009/0215636 A1 | 8/2009 | Krizman et al. | |
| 2014/0005282 A1 | 1/2014 | Krizman et al. | |

FOREIGN PATENT DOCUMENTS

| | | |
|---|---|---|
| EP | 2186879 A2 | 5/2010 |
| JP | 2009524828 A | 7/2009 |
| JP | 2009538430 A | 11/2009 |
| JP | 2010530980 A | 9/2010 |
| WO | 2006127860 A2 | 11/2006 |
| WO | 2008097229 A1 | 8/2008 |
| WO | 2009141141 A1 | 11/2009 |
| WO | 2010053717 A1 | 5/2010 |
| WO | 2011116028 | 9/2011 |

OTHER PUBLICATIONS

Catenacci D.V.T. et al., Absolute quantification of Met using mass spectrometry for clinical application: Assay precision, stability, and correlation with Met gene amplification in FFPE tumor tissue:, PLOS One, vol. 9, No. 7, Jul. 2014 pp. 1-14.
Desouza L.V. et al., "mTRAQ-based quantification of potential endometrial carcinoma biomarkers from archived formalin-fixed paraffin-embedded tissues", Proteomics, Col. 10, No. 17, Sep. 2010, pp. 3108-3116.
Hembrough T. et al., "Selected reaction monitoring (SRM) analysis of epidermal growth factor recepter (EGFR) in formalin fixed tumor tissue", Clin. Proteom., vol. 9, No. 1, 5, May 3, 2012 pp. 1-10.
Hood B Let al.: "Proteomic analysis of formalin-fixed prostate cancer tissue", Molecular & Cellular Proteomics, American Society for Biochemistry and Molecular Biology, vol. 4, No. 11, Nov. 1, 2005, pp. 1741-1753.
Predicted tryptic digest of human c-MET (NCBI Reference Sequence: NP_000236.2) from ExPaSy Peptide Cutter Tool, available online at http://web.expasy.org/peptide_cutter/, Jul. 10, 2015.
Prieto et al., "Liquid Tissue™: proteomic profiling of formalin-fixed tissues", Biotechniques, vol. S6, Jun. 2005, pp. 32-35.

(Continued)

*Primary Examiner* — Robert Yamasaki
(74) *Attorney, Agent, or Firm* — Edell, Shapiro & Finnan, LLC

(57) ABSTRACT

Specific peptides are provided, and derived ionization characteristics of those peptides, from the Hepatocyte Growth Factor Receptor (cMET) protein. The peptides are particularly and surprisingly advantageous for quantifying by the method of Selected Reaction Monitoring (SRM) mass spectrometry the cMET protein directly in biological samples that have been fixed in formalin, or what can also be termed as Multiple Reaction Monitoring (MRM) mass spectrometry. Such biological samples are chemically preserved and fixed where the biological sample is selected from tissues and cells treated with formaldehyde containing agents/fixatives including: formalin-fixed tissue/cells; formalin-fixed/paraffin embedded (FFPE) tissue/cells; FFPE tissue blocks and cells from those blocks; and tissue culture cells that have been formalin fixed and or paraffin embedded. A protein sample is prepared from the biological sample using the Liquid Tissue™ reagents and protocol and the cMET protein is quantitated in the Liquid Tissue™ sample by the method of SRM/MRM mass spectrometry by quantitating in the protein sample at least one or more of the peptides described. These peptides can be quantitated if they reside in a modified or an unmodified form. An example of a modified form of a cMET peptide is phosphorylation of a tyrosine, threonine, serine, and/or other amino acid residues within the peptide sequence.

12 Claims, No Drawings

Specification includes a Sequence Listing.

(56) References Cited

OTHER PUBLICATIONS

Sawada, Krnjiri, et al. "Loss of E-cadherin promotes ovarian cancer metastasis via a5-integrin, which is a therapeutic target." Cancer Research 68.7 (2008): 2329-2339.
Desouza L.V. et al., "Absolute quantification of potential cancer markers in clinical tissue homogenates using multiple reaction monitoring on a hybrid triple quadrupole/linear ion trap tandem mass spectrometer", Anal. Chem., vol. 81, No. 9, May 2009, pp. 3462-3470.
International Search Report and Written Opinion for International Application PCT/US11/67439; dated Apr. 24, 2012; pp. 12.
Supplemental European Search Report for EP11853571.5 dated Feb. 2, 2015, pp. 10.
Supplemental European Search Report for EP11853571.5 dated Jun. 19, 2015, pp. 19.
Geng, M. et al., "Proteomics of Glycoproteins Based on Affinity Selection of Glycopeptides from Tryptic Digests," Journal of Chromatography B, 2001, vol. 752, pp. 293-306.

SEQUENCE LISTING

```
<160> NUMBER OF SEQ ID NOS: 13

<210> SEQ ID NO 1
<211> LENGTH: 25
<212> TYPE: PRT
<213> ORGANISM: Homo sapiens

<400> SEQUENCE: 1
```

```
Ser Asn Ser Glu Ile Ile Cys Cys Thr Thr Pro Ser Leu Gln Gln Leu
1               5                   10                  15

Asn Leu Gln Leu Pro Leu Lys Thr Lys
            20                  25

<210> SEQ ID NO 2
<211> LENGTH: 22
<212> TYPE: PRT
<213> ORGANISM: Homo sapiens

<400> SEQUENCE: 2

Glu Thr Lys Asp Gly Phe Met Phe Leu Thr Asp Gln Ser Tyr Ile Asp
1               5                   10                  15

Val Leu Pro Glu Phe Arg
            20

<210> SEQ ID NO 3
<211> LENGTH: 24
<212> TYPE: PRT
<213> ORGANISM: Homo sapiens

<400> SEQUENCE: 3

Gly His Phe Gly Cys Val Tyr His Gly Thr Leu Leu Asp Asn Asp Gly
1               5                   10                  15

Lys Lys Ile His Cys Ala Val Lys
            20

<210> SEQ ID NO 4
<211> LENGTH: 26
<212> TYPE: PRT
<213> ORGANISM: Homo sapiens

<400> SEQUENCE: 4

Thr Lys Ala Phe Phe Met Leu Asp Gly Ile Leu Ser Lys Tyr Phe Asp
1               5                   10                  15

Leu Ile Tyr Val His Asn Pro Val Phe Lys
            20                  25

<210> SEQ ID NO 5
<211> LENGTH: 21
<212> TYPE: PRT
<213> ORGANISM: Homo sapiens

<400> SEQUENCE: 5

Met Lys Ala Pro Ala Val Leu Ala Pro Gly Ile Leu Val Leu Leu Phe
1               5                   10                  15

Thr Leu Val Gln Arg
            20

<210> SEQ ID NO 6
<211> LENGTH: 20
<212> TYPE: PRT
<213> ORGANISM: Homo sapiens

<400> SEQUENCE: 6

Glu Val Phe Asn Ile Leu Gln Ala Ala Tyr Val Ser Lys Pro Gly Ala
1               5                   10                  15

Gln Leu Ala Arg
            20

<210> SEQ ID NO 7
```

-continued

<211> LENGTH: 14
<212> TYPE: PRT
<213> ORGANISM: Homo sapiens

<400> SEQUENCE: 7

Gly Asp Leu Thr Ile Ala Asn Leu Gly Thr Ser Glu Gly Arg
1               5                   10

<210> SEQ ID NO 8
<211> LENGTH: 11
<212> TYPE: PRT
<213> ORGANISM: Homo sapiens

<400> SEQUENCE: 8

Gln Ile Lys Asp Leu Gly Ser Glu Leu Val Arg
1               5                   10

<210> SEQ ID NO 9
<211> LENGTH: 26
<212> TYPE: PRT
<213> ORGANISM: Homo sapiens

<400> SEQUENCE: 9

Phe Ile Asn Phe Phe Val Gly Asn Thr Ile Asn Ser Ser Tyr Phe Pro
1               5                   10                  15

Asp His Pro Leu His Ser Ile Ser Val Arg
            20                  25

<210> SEQ ID NO 10
<211> LENGTH: 18
<212> TYPE: PRT
<213> ORGANISM: Homo sapiens

<400> SEQUENCE: 10

Ile Thr Asp Ile Gly Glu Val Ser Gln Phe Leu Thr Glu Gly Ile Ile
1               5                   10                  15

Met Lys

<210> SEQ ID NO 11
<211> LENGTH: 11
<212> TYPE: PRT
<213> ORGANISM: Homo sapiens

<400> SEQUENCE: 11

Ala Phe Phe Met Leu Asp Gly Ile Leu Ser Lys
1               5                   10

<210> SEQ ID NO 12
<211> LENGTH: 9
<212> TYPE: PRT
<213> ORGANISM: Homo sapiens

<400> SEQUENCE: 12

Asn Leu Asn Ser Val Ser Val Pro Arg
1               5

<210> SEQ ID NO 13
<211> LENGTH: 9
<212> TYPE: PRT
<213> ORGANISM: Homo sapiens

```
<400> SEQUENCE: 13

Thr Glu Phe Thr Thr Ala Leu Gln Arg
1               5
```

CMET PROTEIN SRM/MRM ASSAY

This application is a continuation of U.S. patent application Ser. No. 13/976,956, filed Jun. 27, 2013, which is a U.S. national stage filing of International Application No. PCT/US11/67439, filed Dec. 27, 2011, which claims the benefit of U.S. Provisional Application No. 61/427,396, filed Dec. 27, 2010, the contents of each of which are hereby incorporated by reference in their entireties. This application also contains a sequence listing submitted electronically via EFS-web, which serves as both the paper copy and the computer readable form (CRF) and consists of a file entitled "001152_8019_US02_SEQ_LISTING", which was created on May 16, 2016, which is 3,271 bytes in size, and which is also incorporated by reference in its entirety.

INTRODUCTION

Specific peptides derived from subsequences of the Hepatocyte Growth Factor Receptor protein referred to as cMET, and also as the HGF/SF receptor, proto-oncogene cMet, scatter factor receptor, and tyrosine-protein kinase Met, are provided. The peptide sequence and fragmentation/transition ions for each peptide are particularly useful in a mass spectrometry-based Selected Reaction Monitoring (SRM) assay(s), which can also be referred to as a Multiple Reaction Monitoring (MRM) assay(s), hereinafter referred to as SRM/MRM assay(s). The use of one such peptide for SRM/MRM quantitative analysis of the cMET protein is described.

This SRM/MRM assay can be used to detect the presence and to measure relative or absolute quantitative levels of one or more of the specific peptides from the cMET protein and therefore provide a means of measuring the amount of the cMET protein in a given protein preparation obtained from a biological sample by mass spectrometry.

The SRM/MRM assays described herein can measure cMET peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by references in their entirety. The methods described in that patent may conveniently be carried out using Liquid Tissue™ reagents and protocol available from Expression Pathology Inc. (Rockville, Md.).

Formaldehyde/formalin fixation of tissues surgically removed from cancer patients is the accepted convention in pathology practice. As a result, formaldehyde/formalin fixed paraffin embedded tissue is the most widely available form of tissues from those patients. Formaldehyde/formalin fixation typically employs aqueous solutions of formaldehyde referred to as formalin. "100%" formalin consists of a saturated solution of formaldehyde (about 40% formaldehyde by volume or 37% by mass) in water, with a small amount of stabilizer, usually methanol to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the cMET protein within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

SUMMARY

The assays described herein measure relative or absolute levels of specific unmodified peptides from the cMET protein and also can measure absolute or relative levels of specific modified peptides from the cMET protein. Examples of modifications include phosphorylated amino acid residues and glycosylated amino acid residues that are present on the peptides.

Relative quantitative levels of the cMET protein are determined by the SRM/MRM methodology, for example by comparing SRM/MRM signature peak areas (e.g., signature peak area or integrated fragment ion intensity) of an individual cMET peptide in different samples (e.g., a control sample and an sample prepared from a patient's tissue). Alternatively, it is possible to compare multiple SRM/MRM signature peak areas for multiple cMET signature peptides, where each peptide has its own specific SRM/MRM signature peak, to determine the relative cMET protein content in one biological sample with the cMET protein content in one or more additional or different biological samples. In this way, the amount of a particular peptide, or peptides, from the cMET protein, and therefore the amount of the cMET protein, is determined relative to the same cMET peptide, or peptides, across 2 or more biological samples under the same experimental conditions. In addition, relative quantitation can be determined for a given peptide, or peptides, from the cMET protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the cMET protein, and therefore the amount of the cMET protein, is determined relative one to another within the same sample. These approaches generate quantitation of an individual peptide, or peptides, from the cMET protein to the amount of another peptide, or peptides, between samples and within samples wherein the amounts as determined by peak area are relative one to another, regardless of the absolute weight to volume or weight to weight amounts of the cMET peptide in the protein preparation from the biological sample. Relative quantitative data about individual signature peak areas between different samples are normalized to the amount of protein analyzed per sample. Relative quantitation can be performed across many peptides from multiple proteins and the cMET protein simultaneously in a single sample and/or across many samples to gain insight into relative protein amounts, one peptide/protein with respect to other peptides/proteins.

Absolute quantitative levels of the cMET protein are determined by, for example, the SRM/MRM methodology whereby the SRM/MRM signature peak area of an individual peptide from the cMET protein in one biological sample is compared to the SRM/MRM signature peak area of a known amount of a "spiked" internal standard. In one embodiment, the internal standard is a synthetic version of the same exact cMET peptide that contains one or more amino acid residues labeled with one or more heavy isotopes. Such isotope labeled internal standards are synthesized so mass spectrometry analysis generates a predictable and consistent SRM/MRM signature peak that is different and distinct from the native cMET peptide signature peak and which can be used as a comparator peak. Thus when the internal standard is spiked in known amounts into a protein or peptide preparation from a biological sample and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer.

Assays of protein levels (e.g., cMET levels) can also be used to diagnose the stage of cancer in a patient or subject diagnosed with cancer by employing the cMET levels. Levels or amounts of proteins or peptides can be defined as the quantity expressed in moles, mass or weight of a protein or peptide determined by the SRM/MRM assay. The level or amount may be normalized to total the level or amount of protein or another component in the lysate analyzed (e.g., expressed in micromoles/microgram of protein or micrograms/microgram of protein). In addition, the level or amount of a protein or peptide may be determined on volume basis, expressed, for example, in micromolar or nanograms/microliter. The level or amount of protein or peptide as determined by the SRM/MRM assay can also be normalized to the number of cells analyzed. Information regarding cMET can thus be used to aid in determining stage or grade of a cancer by correlating the level of the cMET protein (or fragment peptides of the cMET protein) with levels observed in normal tissues.

Once the stage and/or grade, and/or cMET protein expression characteristics of the cancer has been determined, that information can be matched to a list of therapeutic agents (chemical and biological) developed to specifically treat cancer tissue that is characterized by, for example, abnormal expression of the protein or protein(s) (e.g., cMET) that were assayed. Matching information from a cMET protein assay to a list of therapeutic agents that specifically targets, for example, the cMET protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

Certain embodiments of the invention are described below.

1. A method for measuring the level of the Hepatocyte Growth Factor Receptor (cMET) protein in a biological sample, comprising detecting and/or quantifying the amount of one or more modified or unmodified cMET fragment peptides in a protein digest prepared from said biological sample using mass spectrometry; and calculating the level of modified or unmodified cMET protein in said sample; and wherein said level is a relative level or an absolute level.

2. The method of embodiment 1, further comprising the step of fractionating said protein digest prior to detecting and/or quantifying the amount of one or more modified or unmodified cMET fragment peptides.

3. The method of embodiment 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of any of embodiments 1-3, wherein said protein digest of said biological sample is prepared by the Liquid Tissue™ protocol.

5. The method of any of embodiments 1-3, wherein said protein digest comprises a protease digest.

6. The method of embodiment 5, wherein said protein digest comprises a trypsin digest.

7. The method of any of embodiments 1-6, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

8. The method of embodiment 7, wherein the mode of mass spectrometry used is Selected Reaction Monitoring (SRM), Multiple Reaction Monitoring (MRM), and/or multiple Selected Reaction Monitoring (mSRM).

9. The method of any of embodiments 1 to 8, wherein the cMET fragment peptide comprises an amino acid sequence as set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

10. The method of any of embodiments 0-9, wherein the biological sample is a blood sample, a urine sample, a serum sample, an ascites sample, a sputum sample, lymphatic fluid, a saliva sample, a cell, or a solid tissue.

11. The method of embodiment 10, wherein the tissue is formalin fixed tissue.

12. The method of embodiment 10 or 11, wherein the tissue is paraffin embedded tissue.

13. The method of embodiment 10, wherein the tissue is obtained from a tumor.

14. The method of embodiment 13, wherein the tumor is a primary tumor.

15. The method of embodiment 13, wherein the tumor is a secondary tumor.

16. The method of any of embodiments 0 to 15, further comprising quantifying a modified or unmodified cMET fragment peptide.

17. The method of embodiment 16, wherein quantifying the cMET fragment peptide comprises comparing an amount of one or more cMET fragment peptides comprising an amino acid sequence of about 8 to about 45 amino acid residues of cMET as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 in one biological sample to the amount of the same cMET fragment peptide in a different and separate biological sample.

18. The method of embodiment 17, wherein quantifying one or more cMET fragment peptides comprises determining the amount of the each of the cMET fragment peptides in a biological sample by comparison to an added internal standard peptide of known amount, wherein each of the cMET fragment peptides in the biological sample is compared to an internal standard peptide having the same amino acid sequence.

19. The method of embodiment 18, wherein the internal standard peptide is an isotopically labeled peptide.

20. The method of embodiment 19, wherein the isotopically labeled internal standard peptide comprises one or more heavy stable isotopes selected from $^{18}O$, $^{17}O$, $^{34}S$, $^{15}N$, $^{13}C$, $^{2}H$ or combinations thereof.

21. The method of any of embodiments 1 to 20, wherein detecting and/or quantifying the amount of one or more modified or unmodified cMET fragment peptides in the protein digest indicates the presence of modified or unmodified cMET protein and an association with cancer in the subject.

22. The method of embodiment 21, further comprising correlating the results of said detecting and/or quantifying the amount of one or more modified or unmodified cMET fragment peptides, or the level of said cMET protein to the diagnostic stage/grade/status of the cancer.

23. The method of embodiment 22, wherein correlating the results of said detecting and/or quantifying the amount of one or more modified or unmodified cMET fragment peptides, or the level of said cMET protein to the diagnostic stage/grade/status of the cancer is combined with detecting and/or quantifying the amount of other proteins or peptides from other proteins in a multiplex format to provide additional information about the diagnostic stage/grade/status of the cancer.

24. The method of any one of embodiments 1-23, further comprising selecting for the subject from which said biological sample was obtained a treatment based on the presence, absence, or amount of one or more cMET fragment peptides or the level of cMET protein.

25. The method of any one of embodiments 1-24, further comprising administering to the patient from which said biological sample was obtained a therapeutically effective amount of a therapeutic agent, wherein the therapeutic agent and/or amount of the therapeutic agent administered is based upon amount of one or more modified or unmodified cMET fragment peptides or the level of cMET protein.

26. The method of embodiments 24 and 25, wherein therapeutic agents bind the cMET protein and/or inhibit its biological activity.

27. The method of embodiments 1 to 26, wherein the biological sample is formalin fixed tumor tissue that has been processed for quantifying the amount of one or more modified or unmodified cMET fragment peptides employing the Liquid Tissue™ protocol and reagents.

28. The method of any of embodiments 1-27, wherein said one or more modified or unmodified cMET fragment peptides is two or more, three or more, four or more, five or more, six or more, eight or more, or ten or more of the peptides in Table 1.

29. The method of any of embodiments 1-28, comprising quantifying the amount of the peptides in Table 2.

30. A composition comprising one or more, two or more, three or more, four or more, five or more, six or more, eight or more, or ten or more of the peptides in Table 1 or antibodies thereto.

31. The composition of embodiment 30 comprising one or two of the peptides of Table 2 or antibodies thereto.

32. The composition of embodiments 30 or 31, wherein said composition is substantially pure or free of other cellular components selected from any combination of other proteins, membranes lipids and/or nucleic acids.

33. The composition of any of embodiment 30-32, wherein said peptides are isotopically labeled internal standard peptides that comprises one or more, two or more, or three or more, heavy stable isotopes selected from $^{18}O$, $^{17}O$, $^{34}S$, $^{15}N$, $^{13}C$, $^{2}H$ or combinations thereof.

34. The method of embodiments 1-29, further comprising assessing or determining the level (amount) or sequence of one, two, three or more nucleic acid in said protein digest.

35. The method of embodiment 34, wherein the nucleic acids code for, any one or more, any two or more. or all three of cMet, IGF-1R, EGFR, or fragments of any thereof, and/or are antisense sequence of any one or more, any two or more, or all three of cMet, IGF-1R, EGFR or fragments of any thereof.

36. The method of claim 35, wherein said fragments independently have a length greater than about 15, 20, 25, 30, 35, 40 or 50 nucleotides in length.

37. The method of any of embodiments 34-35, wherein assessing or determining the sequence comprises, determining the sequence of nucleotides by one or more sequencing methods, conducting restriction fragment polymorphism analysis, identify deletion, insertions, and/or determining the presence of mutations, including but not limited to, single base pair polymorphisms, transitions and/or transversions.

DETAILED DESCRIPTION

In principle, any predicted peptide derived from cMET protein, prepared for example by digesting with a protease of known specificity (e.g. trypsin), can be used as a surrogate reporter to determine the abundance of cMET protein in a sample using a mass spectrometry-based SRM/MRM assay. Similarly, any predicted peptide sequence containing an amino acid residue at a site that is known to be potentially modified in cMET protein also might potentially be used to assay the extent of modification of cMET protein in a sample.

cMET fragment peptides may be generated by a variety of means including by the use of the Liquid Tissue™ protocol provided in U.S. Pat. No. 7,473,532. The Liquid Tissue™ protocol and reagents are capable of producing peptide samples suitable for mass spectroscopic analysis from formalin fixed paraffin embedded tissue by proteolytic digestion of the proteins in the tissue/biological sample. In the Liquid Tissue™ protocol the tissue/biological is heated in a buffer for an extended period of time at elevated temperatures (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent) and advantageously is a buffer that does not interfere with mass spectrometric analysis. Next the tissue/biological sample is treated with one or more proteases, including but not limited to, trypsin, chymotrypsin, pepsin, and endoproteinase Lys-C for a time sufficient to disrupt the tissue and cellular structure of said biological sample and to liquefy said sample (e.g., a period of time from 30 minutes to 24 hours at a temperature from 37° C. to 65° C.). The result of the heating and proteolysis is a liquid, soluble, dilutable biomolecule lysate.

Once lysates are prepared peptides in the samples may subject to a variety of techniques that facilitate their analysis and measurement by mass spectrometry. In one embodiment, the peptides may be separated by an affinity technique, such as for example immunologically-based purification (e.g., immunoaffinity chromatography), chromatography on ion selective media, or if the peptides are modified, by separation using appropriate media, such as lectins for separation of carbohydrate modified peptides. In one embodiment, the SISCAPA method, which employs immunological separation of peptides prior to mass spectrometric analysis is employed. The SISCAPA technique is described, for example, in U.S. Pat. No. 7,632,686. In other embodiments, lectin affinity methods (e.g., affinity purification and/or chromatography may be used to separate peptides from a lysate prior to analysis by mass spectrometry. Methods for separation of groups of peptides, including lectin-based methods, are described, for example, in Geng et al., J. Chromatography B, 752:293-306 (2001) Immunoaffinity chromatography techniques, lectin affinity techniques and other forms of affinity separation and/or chromatography (e.g., reverse phase, size based separation, ion exchange) may be used in any suitable combination to facilitate the analysis of peptides by mass spectrometry.

Surprisingly, it was found that many potential peptide sequences from the cMET protein are unsuitable or ineffective for use in mass spectrometry-based SRM/MRM assays for reasons that are not immediately evident. In particular it was found that many tryptic peptides from the cMet protein could not be detected efficiently or at all in a Liquid Tissue lysate from formalin fixed, paraffin embedded tissue. As it was not possible to predict the most suitable peptides for MRM/SRM assay, it was necessary to experimentally identify modified and unmodified peptides in actual Liquid Tissue™ lysates to develop a reliable and accurate SRM/MRM assay for the cMET protein. While not wishing to be bound by any theory, it is believed that some peptides might, for example, be difficult to detect by mass spectrometry as they do not ionize well or produce fragments distinct from other proteins, peptides may also fail to resolve well in separation (e.g., liquid chromatography), or adhere to glass or plastic ware. Accordingly, those peptides from the cMet protein that can be detected in a Liquid Tissue lysate (e.g., the peptides in Tables 1 and 2) prepared from a formalin fixed tissue sample are the peptides for which SRM/MRM assays can be employed in a cMet SRM/MRM assay.

cMET peptides found in various embodiments of this disclosure (e.g., Tables 1 and 2) were derived from the cMET protein by protease digestion of all the proteins within a complex Liquid Tissue™ lysate prepared from cells procured from formalin fixed cancer tissue. Unless noted otherwise, in each instance the protease was trypsin. The Liquid Tissue™ lysate was then analyzed by mass spectrometry to determine those peptides derived from the cMET protein that are detected and analyzed by mass spectrometry. Identification of a specific preferred subset of peptides for mass-spectrometric analysis is based on: 1) experimental determination of which peptide or peptides from a protein ionize in mass spectrometry analyses of Liquid Tissue™ lysates; and 2) the ability of the peptide to survive the protocol and experimental conditions used in preparing a Liquid Tissue™ lysate. This latter property extends not only to the amino acid sequence of the peptide but also to the ability of a modified amino acid residue within a peptide to survive in modified form during the sample preparation.

TABLE 1

| Peptide | Peptide Sequence |
|---|---|
| SEQ ID NO: 1 | SNSEIICCTTPSLQQLNLQLPLKTK |
| SEQ ID NO: 2 | ETKDGFMFLTDQSYIDVLPEFR |
| SEQ ID NO: 3 | GHFGCVYHGTLLDNDGKKIHCAVK |
| SEQ ID NO: 4 | TKAFFMLDGILSKYFDLIYVHNPVFK |
| SEQ ID NO: 5 | MKAPAVLAPGILVLLFTLVQR |
| SEQ ID NO: 6 | EVFNILQAAYVSKPGAQLAR |
| SEQ ID NO: 7 | GDLTIANLGTSEGR |
| SEQ ID NO: 8 | QIKDLGSELVR |
| SEQ ID NO: 9 | FINFFVGNTINSSYFPDHPLHSISVR |
| SEQ ID NO: 10 | ITDIGEVSQFLTEGIIMK |
| SEQ ID NO: 11 | AFFMLDGILSK |
| SEQ ID NO: 12 | NLNSVSVPR |
| SEQ ID NO: 13 | TEFTTALQR |

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 11 | AFFMLDGILSK | 1241.65986 | 2 | 621.333008 | 632.3608 | y6 |
| | | | 2 | 621.333008 | 745.4449 | y7 |
| | | | 2 | 621.333008 | 876.4854 | y8 |
| | | | 2 | 621.333008 | 1023.554 | y9 |
| | | | 2 | 621.333008 | 1170.622 | y10 |
| | | | 2 | 621.333008 | 1241.659 | y11 |
| SEQ ID NO: 12 | NLNSVSVPR | 985.54252 | 2 | 493.273987 | 557.34 | y5 |
| | | | 2 | 493.273987 | 644.3721 | y6 |
| | | | 2 | 493.273987 | 758.415 | y7 |
| | | | 2 | 493.273987 | 871.499 | y8 |
| | | | 2 | 493.273987 | 985.542 | y9 |

Protein lysates from cells procured directly from formalin (formaldehyde) fixed tissue were prepared using the Liquid Tissue™ reagents and protocol that entails collecting cells into a sample tube via tissue microdissection followed by heating the cells in the Liquid Tissue™ buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue™ lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is employed. Ion trap mass spectrometers however may be the best type of mass spectrometer for conducting global profiling of peptides. Although SRM/MRM assay can be developed and performed on any type of mass spectrometer, including a MALDI, ion trap, or triple quadrupole, the most advantageous instrument platform for SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue™ lysates, and the very large list of peptides was collated into a single dataset. That type of dataset can be considered to represent the peptides that can be detected in the type of biological sample that was analyzed (after protease digestion), and specifically in a Liquid Tissue™ lysate of the biological sample, and thus includes the peptides for specific proteins, such as for example the cMET protein.

In one embodiment, the cMET tryptic peptides identified as useful in the determination of absolute or relative amounts of the cMET receptor include one or more, two or more, three or more, four or more, five or more, six or more, eight or more, or ten or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, each of which are listed in Table 1. Each of those peptides was detected by mass spectrometry in Liquid Tissue™ lysates prepared from formalin-fixed, paraffin embedded tissue. Thus, each of the peptides in Table 1, or any combination of those peptides (e.g., one or more, two or more, three or more, four or more, five or more, six or more, eight or more, or ten or more of those peptides recited in Table 1, and particularly combinations with the peptides found in Table 2) are candidates for use in quantitative SRM/MRM assay for the cMET protein in human biological samples, including directly in formalin fixed patient tissue.

The cMET tryptic peptides listed in Table 1 include those detected from multiple Liquid Tissue™ lysates of multiple different formalin fixed tissues of different human organs including prostate, colon, and breast. Each of those peptides is considered useful for quantitative SRM/MRM assay of the cMET protein in formalin fixed tissue. Further data analysis of these experiments indicated no preference is observed for any specific peptides from any specific organ site. Thus, each of these peptides is believed to be suitable for conducting SRM/MRM assays of the cMET protein on a Liquid Tissue™ lysate from any formalin fixed tissue originating from any biological sample or from any organ site in the body.

In one embodiment the peptides in Table 1, or any combination of those peptides (e.g., one or more, two or more, three or more, four or more, five or more, six or more, eight or more, or ten or more of those peptides recited in Table 1, and particularly combinations with the peptides also found in Table 2) are assayed by methods that do not rely upon mass spectroscopy, including, but not limited to, immunological methods (e.g., Western blotting or ELISA). Regardless of how information directed to the amount of the peptide(s) (absolute or relative) is obtained, the information may be employed in any of the methods described herein, including indicating (diagnosing) the presence of cancer in a subject, determining the stage/grade/status of the cancer, providing a prognosis, or determining the therapeutics or treatment regimen for a subject/patient.

Embodiments of the present disclosure include compositions comprising one or more, two or more, three or more, four or more, five or more, six or more, eight or more, or ten or more of the peptides in Table 1. In some embodiments, the compositions comprise the peptides in Table 2. Compositions comprising peptides may include one or more, two or more, three or more, four or more, five or more, six or more, eight or more, or ten or more peptides that are isotopically labeled. Each of the peptides may be labeled with one or more isotopes selected independently from the group consisting of: $^{18}O$, $^{17}O$, $^{34}S$, $^{15}N$, $^{13}C$, $^{2}H$ or combinations thereof. Compositions comprising peptides from the cMET protein, whether isotope labeled or not, do not need to contain all of the peptides from that protein (e.g., a complete set of tryptic peptides). In some embodiments the compositions do not contain one or more, two or more, three or more, four or more, five or more, six or more, eight or more, or ten or more peptides from cMET, and particularly peptides appearing in Table 1 or Table 2. Compositions comprising peptides may be in the form of dried or lyophized materials, liquid (e.g., aqueous) solutions or suspensions, arrays, or blots.

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement SRM/MRM assay for each peptide derived from the cMET protein it is desirable to utilize information in addition to the peptide sequence in the analysis. That additional information may be used in directing and instructing the mass spectrometer (e.g. a triple quadrupole mass spectrometer), to perform the correct and focused analysis of specific targeted peptide(s), such that the assay may be effectively performed.

The additional information about target peptides in general, and about specific cMET peptides, may include one or more of the mono isotopic mass of each peptide, its precursor charge state, the precursor m/z value, the m/z transition ions, and the ion type of each transition ion. Additional peptide information that may be used to develop an SRM/MRM assay for the cMET protein is shown by example for two (2) of the cMET peptides from the list in Table 1 and is shown in Table 2. Similar additional information described for these two (2) cMET peptides shown by example in Table 2 may be prepared, obtained, and applied to the analysis of the other peptides contained in Table 1.

The method described below was used to: 1) identify candidate peptides from the cMET protein that can be used for a mass spectrometry-based SRM/MRM assay for the cMET protein, 2) develop individual SRM/MRM assay, or assays, for target peptides from the cMET protein in order to correlate and 3) apply quantitative assays to cancer diagnosis and/or choice of optimal therapy.

ASSAY METHOD

1. Identification of SRM/MRM Candidate Fragment Peptides for the cMET Protein
   a. Prepare a Liquid Tissue™ protein lysate from a formalin fixed biological sample using a protease or proteases, (that may or may not include trypsin), to digest proteins
   b. Analyze all protein fragments in the Liquid Tissue™ lysate on an ion trap tandem mass spectrometer and identify all fragment peptides from the cMET protein, where individual fragment peptides do not contain any peptide modifications such as phosphorylations or glycosylations
   c. Analyze all protein fragments in the Liquid Tissue™ lysate on an ion trap tandem mass spectrometer and identify all fragment peptides from the cMET protein that carry peptide modifications such as for example phosphorylated or glycosylated residues
   d. All peptides generated by a specific digestion method from the entire, full length cMET protein potentially can be measured, but preferred peptides used for development of the SRM/MRM assay are those that are identified by mass spectrometry directly in a complex Liquid Tissue™ protein lysate prepared from a formalin fixed biological sample
   e. Peptides that are specifically modified (phosphorylated, glycosylated, etc.) in patient tissue and which ionize, and thus can be detected, in a mass spectrometer when analyzing a Liquid Tissue™ lysate from a formalin fixed biological sample are identified as candidate peptides for assaying peptide modifications of the cMET protein
2. Mass Spectrometry Assay for Fragment Peptides from cMET Protein
   a. SRM/MRM assay on a triple quadrupole mass spectrometer for individual fragment peptides identified in a Liquid Tissue™ lysate is applied to peptides from the cMET protein
      i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
      ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
      iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
   b. Perform SRM/MRM analysis so that the amount of the fragment peptide of the cMET protein that is detected, as a function of the unique SRM/MRM signature peak area from an SRM/MRM mass spectrometry analysis, can indicate both the relative and absolute amount of the protein in a particular protein lysate.
      i. Relative quantitation may be achieved by:
         1. Determining increased or decreased presence of the cMET protein by comparing the SRM/MRM signature peak area from a given cMET peptide detected in a Liquid Tissue™ lysate from one formalin fixed biological sample to the same SRM/MRM signature peak area of the same cMET fragment peptide in at least a second, third, fourth or more Liquid Tissue™ lysates from least a second, third, fourth or more formalin fixed biological samples
         2. Determining increased or decreased presence of the cMET protein by comparing the SRM/MRM signature peak area from a given cMET peptide detected in a Liquid Tissue™ lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
         3. Determining increased or decreased presence of the cMET protein by comparing the SRM/MRM signature peak area for a given cMET peptide to the SRM/MRM signature peak areas from other fragment peptides derived from different proteins within the same Liquid Tissue™ lysate from the formalin fixed biological sample in order to normalize changing levels of cMET protein to levels of other proteins that do not change their levels of expression under various cellular conditions.
         4. These assays can be applied to both unmodified fragment peptides and for modified fragment peptides of the cMET protein, where the modifications include, but are not limited to, phosphorylation and/or glycosylation, and where the relative levels of modified peptides are determined in the same manner as determining relative amounts of unmodified peptides.
      ii. Absolute quantitation of a given peptide may be achieved by comparing the SRM/MRM signature peak area for a given fragment peptide from the cMET protein in an individual biological sample to the SRM/MRM signature peak area of an internal fragment peptide standard spiked into the protein lysate from the biological sample
         1. The internal standard is a labeled synthetic version of the fragment peptide from the cMET protein that is being interrogated. This standard is spiked into a sample in known amounts, and the SRM/MRM signature peak area can be determined for both the internal fragment peptide standard and the native fragment peptide in the biological sample separately, followed by comparison of both peak areas
2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Apply Fragment Peptide Quantitation to Cancer Diagnosis and Treatment
   a. Perform relative and/or absolute quantitation of fragment peptide levels of the cMET protein and demonstrate that the previously-determined association, as well understood in the field of cancer, of cMET protein expression to the stage/grade/status of cancer in patient tumor tissue is confirmed
   b. Perform relative and/or absolute quantitation of fragment peptide levels of the cMET protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy Assessment of cMET protein levels in tissues based on analysis of formalin fixed patient-derived tissue can provide diagnostic, prognostic, and therapeutically-relevant information about each particular patient. In one embodiment, this disclosure describes a method for measuring the level of the cMET protein in a biological sample, comprising detecting and/or quantifying the amount of one or more modified or unmodified cMET fragment peptides in a protein digest prepared from said biological sample using mass spectrometry; and calculating the level of modified or unmodified cMET protein in said sample; and wherein said level is a relative level or an absolute level. In a related embodiment, quantifying one or more cMET fragment peptides comprises determining the amount of the each of the cMET fragment peptides in a biological sample by comparison to an added internal standard peptide of known amount, wherein each of the cMET fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the cMET protein in a biological sample described herein (or fragment peptides as surrogates thereof) may be used as a diagnostic indicator of cancer in a patient or subject. In one embodiment, the results from measurements of the level of the cMET protein may be employed to determine the diagnostic stage/grade/status of a cancer by correlating (e.g., comparing) the level of cMET receptor found in a tissue with the level of that protein found in normal and/or cancerous or precancerous tissues.

Because both nucleic acids and protein can be analyzed from the same Liquid Tissue biomolecular preparation it is possible to generate additional information about disease diagnosis and drug treatment decisions from the same sample. For example, the cMet protein is a tyrosine kinase receptor that is capable of stimulating uncontrolled cell growth (cancer) by activation of specific cell signal protein pathways. If cMet is expressed by certain cells to at increased levels, when assayed by SRM can provide information about the state of the cells and their potential for uncontrolled growth and the development of cancers can be obtained.

Other receptor tyrosine kinases, such as IGF-1R and EGFR, can also perform the same role as cMet in cells. Each of those three proteins can signal for uncontrolled cell growth through related cell signal pathways, and each can provide drug resistance to a cell that is receiving targeted therapy for one of these proteins. It is therefore advantageous to analyze for the presence of any combination, or all three, of those proteins simultaneously to determine if over expression or mutations leading to tyrosine kinase activity have arisen in the cells.

In one embodiment, SRM/MRM assays of any two or more of cMet, IGF-1R and/or EGFR, are conducted in conjunction with one or more assays to determine whether or not one, two or all three of those proteins are activated, and can give rise drug resistance. Such assays include assessing the sequence of the nucleic acids (e.g., DNA, RNA or cDNA) coding for those proteins to determine if mutations associated with increased tyrosine kinase activity are present in the cells used to generate the peptide lysates used for SRM/MRM analysis. For example, in one embodiment the nucleic acid mutation status of the activation sight of the EGFR protein is important to treatment decisions with anti-EGFR therapeutic agents. Thus by providing nucleic acid and protein analysis of both the protein status and the mutation status in the same Liquid Tissue preparation much more information can be gained for making decisions about treatment strategy, and advantageously from the same sample. In another embodiment, SRM/MRM assays of cMet can be conducted while conducting mutational analysis IGF-1R and/or EGFR using nucleic acids from the same lysate.

The above description and exemplary embodiments of methods and compositions are illustrative of the scope of the present disclosure. Because of variations which will be apparent to those skilled in the art, however, the present disclosure is not intended to be limited to the particular embodiments described above.

The invention claimed is:

1. A method for measuring the level of the Hepatocyte Growth Factor Receptor (cMET) protein in a human biological sample, comprising detecting and quantifying the amount of a cMET fragment peptide in a protein digest prepared from said human biological sample using mass spectrometry; wherein the cMET fragment peptide is SEQ ID NO:13, and calculating the level of modified or unmodified cMET protein in said sample; and wherein said level is a relative level or an absolute level.

2. The method of claim 1, further comprising the step of fractionating said protein digest prior to detecting and quantifying the amount of said cMET fragment peptide.

3. The method of claim 1, wherein said protein digest comprises a protease digest.

4. The method of claim 1, wherein the biological sample is paraffin embedded tissue.

5. The method of claim 1, wherein the biological sample is tissue obtained from a tumor.

6. The method of claim 1, wherein quantifying the cMET fragment peptide comprises comparing an amount of said cMET fragment peptide in one biological sample to the amount of the same cMET fragment peptide in a different and separate biological sample.

7. The method of claim 1, wherein quantifying said cMET fragment peptide comprises determining the amount of said cMET fragment peptide in a biological sample by comparison to an added internal standard peptide of known amount, wherein said cMET fragment peptide in the biological sample is compared to an internal standard peptide having the same amino acid sequence, and wherein the internal standard peptide is an isotopically labeled peptide.

8. The method of claim 1, wherein detecting and quantifying the amount of said cMET fragment peptide in the protein digest indicates the presence of modified or unmodified cMET protein and an association with cancer in the subject.

9. The method of claim 8, further comprising correlating the results of said detecting and quantifying the amount of said cMET fragment peptide, or the level of said cMET protein to the diagnostic stage/grade/status of the cancer.

10. The method of claim 9, wherein correlating the results of said detecting and quantifying the amount of said cMET fragment peptide, or the level of said cMET protein to the diagnostic stage/grade/status of the cancer is combined with detecting and/or quantifying the amount of other proteins or peptides from other proteins in a multiplex format to provide additional information about the diagnostic stage/grade/status of the cancer.

11. The method of claim 1, further comprising administering to the patient from which said biological sample was obtained a therapeutically effective amount of a therapeutic agent, wherein the therapeutic agent and/or amount of the therapeutic agent administered is based upon the amount of said cMET fragment peptide or the level of cMET protein.

12. The method of claim 11, wherein said therapeutic agent inhibits the biological activity of the cMET protein.

* * * * *